United States Patent [19]

Cook et al.

[11] 4,447,570
[45] May 8, 1984

[54] BINDER COMPOSITIONS FOR MAKING NONWOVEN FABRICS HAVING GOOD HYDROPHOBIC REWET PROPERTIES

[75] Inventors: Gerald R. Cook, Wyomissing; John G. Iacoviello, Allentown; Robert K. Pinschmidt, Jr., Allentown; George Davidowich, Allentown, all of Pa.

[73] Assignee: Air Products and Chemicals, Inc., Allentown, Pa.

[21] Appl. No.: 353,445

[22] Filed: Mar. 1, 1982

[51] Int. Cl.$^3$ .......................... B32B 5/16; D04H 1/58
[52] U.S. Cl. ................................. 524/127; 156/327; 156/334; 428/288; 523/111; 524/564; 604/365; 604/367; 604/378
[58] Field of Search ............... 524/127, 564; 523/111; 156/327, 334; 128/288; 604/365, 367, 378; 428/288

[56] References Cited

U.S. PATENT DOCUMENTS

| | | | |
|---|---|---|---|
| 2,758,102 | 8/1958 | Grummitt et al. | 524/413 |
| 3,137,588 | 6/1964 | Taylor | 428/452 |
| 3,536,518 | 10/1970 | Drelich | 427/283 |
| 3,642,740 | 2/1972 | Pierce, Jr. | 526/193 |
| 3,649,330 | 3/1972 | Drelich | 427/288 |
| 3,922,462 | 11/1975 | Katz et al. | 428/290 |
| 4,084,033 | 4/1978 | Drelic | 428/198 |
| 4,290,931 | 9/1981 | Holken et al. | 524/123 |
| 4,364,992 | 12/1982 | Ito et al. | 428/288 |

*Primary Examiner*—Ronald W. Griffin
*Attorney, Agent, or Firm*—Michael Leach; E. Eugene Innis; James C. Simmons

[57] ABSTRACT

A binder composition for nonwoven fabrics which comprises
(a) a fugitive base salt of a phosphate ester surfactant or a carboxylate surfactant,
(b) a latex comprising a vinyl acetate-ethylene-olefinically unsaturated carboxylic acid interpolymer colloidally suspended in water, the interpolymer containing about 0.5 to 7.0 weight percent olefinically unsaturated carboxylic acid and sufficient ethylene to provide the interpolymer with a glass transition temperature of from about −30° to +20° C., and
(c) a polyvalent metal complex compound comprising a polyvalent metal ion and counter ions or ligands which hinder interaction of the polyvalent metal ion with the carboxylate and phosphate groups of the surfactant and interpolymer at room temperature, but at elevated temperature permit such interaction because the counter ions or ligands are expelled or are replaced by the anionic group of the surfactant and interpolymer.

Nonwoven fabrics, particularly diaper innerliners, bonded with such binder compositions possess good dry and wet tensile strengths and good low rewet properties.

34 Claims, No Drawings

4,447,570

BINDER COMPOSITIONS FOR MAKING NONWOVEN FABRICS HAVING GOOD HYDROPHOBIC REWET PROPERTIES

TECHNICAL FIELD

This invention relates to binder compositions for bonding together a loosely assembled mass of fibers into a nonwoven fabric. More particularly, this invention relates to binder compositions comprising a resin emulsion containing an anionic surfactant, and a polyvalent metal compound.

BACKGROUND OF THE INVENTION

Nonwoven fabrics or materials comprise loosely assembled webs or masses of fibers bound together with an adhesive binder. Adequately bonded nonwoven fabrics have a variety of uses including the preparation of nonwoven innerliners for baby diapers and other products. It is known to form bonded nonwoven fabrics by impregnating, printing or otherwise depositing an adhesive bonding composition on a base web predominantly comprising relatively long fibers, including those of textile length of from about one-half inch (1.27 cm) to about 2 and one-half inches (6.35 cm), or more. These fibers may be of cellulosic or polymeric materials such as polyesters, polyamides, polyacrylates and the like. The base web of nonwoven fibers, to which the binder composition is applied, can be produced by carding, garnetting, air laying, paper making procedures, or other known operations.

With respect to disposable baby diapers and related products, a large market for nonwoven components of these products has developed because of their improved performance, comfort and convenience. Regarding comfort, an important function of diaper construction is keeping moisture away from an infant's skin while at the same time handling a full volume discharge of urine.

A disposable diaper typically comprises a fibrous innerliner which contacts the infant's skin, a layer of highly porous, loosely compacted cellulosic wadding, a paper-like, densified, highly compacted cellulosic fibrous layer integral with the loosely compacted wadding and an impervious backing sheet adhered to the densified layer throughout their interface. The innerliner normally is comprised of fibers, especially polyester fibers, that are held together by a binder. The innerliner is of porous construction and its fibers have less wettability for water than the fibers of the loosely compacted wadding, resulting in a tendency for liquid to flow from the facing web into the wadding.

Two important characteristics of nonwoven innerliners are strikethrough and rewet. Strikethrough is the ability of the innerliner to pass moisture into the wadding upon initial contact. Rewet is the tendency of moisture to move back through the innerliner after initial wetting. Low rewet, or hydrophobic rewet, is needed to keep moisture away from the infant's skin.

It is customary that the binder for the nonwoven innerliner also contains a wetting agent (strikethrough surfactant) which reduces the water repellency of the innerliner so that urine may readily pass through it and into the loosely compacted wadding. The passage of the urine through the innerliner extracts most of the water soluble wetting agents from the binder rendering the innerliner substantially impervious to rewetting.

Thus, the innerliner separating the cellulosic wadding from the infant must be strong both wet and dry, i.e., high wet and dry tensile strength, possess good strikethrough and demonstrate low rewet properties.

Current emulsion binders used to bond the nonwoven polyester fibers of diaper innerliners are typically deficient in one or more properties. For example, N-methylolacrylamide based emulsions produce high residual levels of formaldehyde in the final innerliner product. Acrylate based emulsions typically show blocking. Styrene-butadiene based emulsions often show yellowing, insufficient softness, odor and running problems. Vinyl acetate-ethylene based emulsions without an added crosslinker such as N-methylolacrylamide typically have poor wet tensiles and poor rewet.

U.S. Pat. No. 3,922,462 discloses a permanently absorbent nonwoven fabric comprising a web of fibers, a crosslinkable latex binder and a surfactant consisting of at least one bis-alkyl sulfosuccinate having alkyl substituents containing 13-14 carbon atoms.

The incorporation of acrylic acid and other carboxylic acid containing monomers into interpolymers is well known. Crosslinking with metal ions including aluminum and zirconium has previously been disclosed as being useful for the insolubilization of carboxylic acid group containing materials such as polyacrylic acid and starches containing carboxylic acid groups. U.S. Pat. Nos. 2,758,102 and 3,137,588 are illustrative.

In addition, the use of metal ions in resin compositions which can be deposited on other materials in a controlled manner are disclosed in U.S. Pat. Nos. 3,536,518; 3,649,330 and 4,084,033.

U.S. Pat. No. 3,536,518 discloses an aqueous resin binder dispersion which is stable at a pH of from about 7 to about 9. The binder dispersion is dispersed and stabilized by an anionic surfactant which is active at a pH from about 7 to about 9 but which is inactivated by the presence of free divalent or trivalent metal cations which are released at pH less than about 7 by a metal chelate having a divalent or trivalent cation. By substantially simultaneously applying the binder dispersion to a fibrous material and lowering its pH to less than 7, the binder material is precipitated onto the fibrous material. The anionic surfactant is selected from the class consisting of alkyl aromatic sulfonic acids, alkane sulfonic acids and carboxylic acids.

U.S. Pat. No. 3,649,330 discloses a composition of an emulsion polymerized resin, which has a pH of less than 7, and certain metal salts, wherein the metal ion has a valence of at least 3, and a method of controlling resin deposition on materials by pretreating the materials whereby they have an alkaline condition and by applying the composition to the material under alkaline conditions.

U.S. Pat. No. 4,084,033 discloses a method of depositing synthetic resins from their colloidal aqueous dispersions onto wet fibrous webs to form bonded fibrous nonwoven fabrics comprising the use of (1) metal complex coordination compounds and (2) synthetic resins and/or surfactants, at least one of which contains a specific coordinating ligand capable of being affected by ions of said metals to control the total migration of the resin binder during such deposition. The surfactants are those anionic surfactants disclosed in U.S. Pat. No. 3,536,518.

The use of phosphate ester surfactants in emulsion polymerization is also known. Representative of such art are U.S. Pat. No. 3,642,740; U.S. Pat. No. 4,290,931 and Ger. Offen. No. 2,533,043.

There is no teaching in this prior art with regard to binder compositions which afford nonwoven products having good tensiles and good low rewet characteristics.

SUMMARY OF THE INVENTION

It has now been discovered that bonded nonwoven products having good dry and wet tensile strength and a good low rewet property can be achieved by the use of a binder emulsion composition containing particular anionic surfactants and polyvalent metal compounds.

The invention pertains to a binder composition for a nonwoven fabric formed from a loosely assembled web of fibers. The binder composition comprises an anionic immobilizable surfactant, a latex comprising a vinyl acetate-ethylene-olefinically unsaturated carboxylic acid interpolymer colloidally suspended in water, the interpolymer containing about 0.5 to 7.0 wt. % olefinically unsaturated carboxylic acid and sufficient ethylene to provide the interpolymer with a glass transition temperature (Tg) of from about $-30°$ to $+20°$ C.; and a polyvalent metal complex compound, whose polyvalent metal ion acts as a crosslinking agent for the carboxylic acid.

The term "anionic immobilizable surfactant" means a surfactant which can interact with the polyvalent metal ion such that the surfactant becomes bound, affixed to, or immobilized by the polyvalent metal ion. Anionic immobilizable surfactants suitable for use in the invention are free carboxylic acid group containing surfactants and phosphate ester surfactants.

However, the phosphate ester surfactant is most desirably added to the composition in a form having its acidic proton neutralized with a fugitive base. In other words, the cationic counter ion of the surfactant is ideally a protonated fugitive base, a fugitive base being a base which can be expelled thermally or by evaporation leaving the free acid form of the anionic immobilizable surfactant. Examples of suitable fugitive bases include ammonia and amines such as the methylamines, pyridine, ethylamines, hydroxylamines, morpholine, hydrazine, and the like.

The preferred free carboxylic acid group containing surfactants are the sulfoalkanedioic acid half-esters, particularly the sulfosuccinic acid half-esters. These surfactants may be added as the alkali or fugitive base salt, preferably the latter.

The preferred phosphate ester surfactants are the phosphate esters of poly(oxyalkylene)alcohols such as, for example, poly(oxyethylene) and poly(oxypropylene) alcohols. Especially desirable are the phosphate esters of alkyl or alkylaryl poly(oxyalkylene)alcohol ethers.

As an advantage of the invention, nonwoven fibers, particularly the polyester fibers, saturatingly bonded with such binder compositions possess the following important features: good tensile strengths of the coated fiber web, both dry and wet, and unexpectedly superior low rewet properties compared to binder composition containing other surfactants. These features are achieved by the combination of the vinyl acetate-ethylene-olefinically unsaturated carboxylic acid interpolymer, the polyvalent metal compound and, most importantly, the anionic immobilizable surfactant, such as a phosphate ester or carboxylate surfactant.

A preferred embodiment of the invention is the nonwoven innerliner of a diaper or incontinent pad saturatingly bonded with the above described surfactant, interpolymer latex and polyvalent metal compound.

DETAILED DESCRIPTION OF THE INVENTION

The invention provides nonwoven fabrics, particularly diaper innerliners, with the very desirable properties of good dry and wet tensile strengths and good low rewet by the use of a binder composition comprising a polyvalent metal complex compound, a vinyl acetate-ethylene-olefinically unsaturated carboxylic acid interpolymer latex and an anionic immobilizable surfactant, which preferably is a phosphate ester surfactant or a carboxylate surfactant, such as a sulfoalkanedioic acid half-ester surfactant, particularly a sulfosuccinate half-ester surfactant.

The surfactant may be added to the latex prior to, intermittently or continously during, or after the emulsion polymerization of vinyl acetate monomer and an olefinically unsaturated carboxylic acid monomer under an ethylene pressure. It is much preferred that at least a portion of the surfactant addition be present during polymerization in order to obtain much superior hydrophobic rewet properties. The phosphate ester surfactant is preferably added as a fugitive base salt because the free acid form has limited solubility and an alkali metal salt, such as the sodium salt, does not give as good hydrophobic rewet properties. For example, the free acid of the phosphate ester surfactant may be added to water and the pH adjusted to about 4–6 with ammonium hydroxide to provide an aqueous solution of the fugitive base salt for addition to the latex or a premix for the polymerization reaction.

The anionic immobilizable surfactant may be used alone or in combination with various other emulsifying and/or wetting agents.

To the resultant interpolymer emulsion containing an anionic immobilizable surfactant is added a polyvalent metal complex compound for the heat curing, at an elevated temperature, of a fiber web padded with the composition. More specifically, the nonwoven fabric is bonded together with a binder composition which comprises a latex comprising an anionic immobilizable surfactant, ideally a phosphate ester surfactant or a sulfoalkanedioic acid half-ester surfactant, and a vinyl acetate-ethylene-olefinically unsaturated carboxylic acid interpolymer dispersed in water, the interpolymer containing about 0.5 to 7.0 wt % olefinically unsaturated carboxylic acid and sufficient ethylene to provide the interpolymer with a glass transition temperature of from about $-30°$ to $+20°$ C., and a polyvalent metal compound for crosslinking the carboxylic acid and interacting with the surfactant.

The olefinically unsaturated carboxylic acid monomer is preferably added incrementally during the polymerization reaction.

The preferred olefinically unsaturated carboxylic acid monomers are the alpha,beta unsaturated carboxylic acids.

The polyvalent metal complex compound is a water soluble compound of a polyvalent metal ion having counter ions or ligands which hinder the interaction of the polyvalent metal ion with the carboxylate or phosphate groups of the surfactant and the carboxylate groups of the interpolymer at room temperature, but at elevated temperature encountered during drying or curing, permit such metal ion-surfactant and/or metal ion-interpolymer interaction because the counter ion or ligand is driven off or is replaced by the anionic groups of the surfactant and interpolymer.

Without wishing to be held to a particular theory, we believe the efficacious action of the binder compositions of this invention to yield nonwoven materials having good tensiles and low rewet is a combination of several factors. The use of a vinyl acetate-ethylene base polymer gives a soft, flexible and hydrophobic backbone to the polymer. The proper choice of glass transition temperature (Tg), i.e. percent ethylene, is important to the proper balance of softness, strength and hydrophobicity. Hydrophobicity is required to minimize binder swelling and tensile loss in water and to minimize rewet, the tendency of moisture to migrate out of the cellulosic wadding back through the innerliner.

By incorporating an olefinically unsaturated, preferably an alpha,beta unsaturated, carboxylic acid comonomer into the vinyl acetate-ethylene base polymer to both hydrogen bond with itself and to act as a site for crosslinking with the added polyvalent metal ion, the necessary dry and wet tensile strengths are achieved.

Most surprisingly, the good rewet properties are largely provided by the anionic immobilizable surfactant upon combination with the polyvalent metal ion such as zirconium or aluminum. It is speculated that the polyvalent metal ion and the immobilizable surfactant form water insoluble complexes during cure. However, it is necessary that the polyvalent metal compound and the surfactant and interpolymer be able to coexist in the binder composition at room temperatures without causing the emulsion composition to break down or otherwise adversely affect performance.

Generally, the interpolymer in binder compositions of this invention may contain vinyl acetate in an amount ranging from about 60 to 95 wt %, preferably about 75 to 85 wt %, based on the interpolymer.

The amount of ethylene in the interpolymer to give the desired glass transition temperature of about −30° to +20° C. is controlled by the ethylene pressure during the polymerization reaction. Such practice is well within the skill of an ordinary worker in the art. It is preferred that the polymer glass transition temperature be from about −5° to +15° C. An example of an effective ethylene pressure to produce the desired glass transition temperature is about 650 psi (44.2 atm) at 50° C.

Desirably, the carboxylic acid comonomers useful in preparing the interpolymer of the binder compositions of the invention are those alpha,beta unsaturated carboxylic acid compounds typically used in emulsion polymerization although other olefinically unsaturated carboxylic acid monomers, such as 3-butenoic acid, acrylamidohydroxyacetic acid and acrylamidoacetic acid, may be used. Representative of such alpha,beta unsaturated carboxylic acid comonomers are acrylic acid, crotonic acid, isocrotonic acid, methacrylic acid, sorbic acid, cinnamic acid, maleic acid and the anhydride, fumaric acid, and itaconic acid. Additional useful carboxylic acid comonomers include maleate and fumarate monoesters. Crotonic acid and acrylic acid are the preferred carboxylic acid comonomers for use in the invention with the latter being most preferred. While the amount of the carboxylic acid comonomer in the interpolymer may range from about 0.5 to 7.0 wt %, there appears to be no additional advantage to levels above 5%. Accordingly, the preferred range is from about 1 to 5 wt %.

The olefinically unsaturated sulfonic acids typically used in polymerization recipes, such as vinyl sulfonic acid, allylsulfonic acid, acrylamidopropanesulfonic acid and the like may be added in small amounts to the polymerization reaction.

Optionally, small amounts of crosslinking comonomers such as diallyl maleate, diallyl phthalate, and triallyl cyanurate may also be used to further improve wet tensile strengths and rewet characteristics. The addition of from 0.5 to 5 wt % of other reactive comonomers, such as acrylamide, hydroxyethyl acrylate and alkylated and hydroxyalkylated acrylamides is also within the scope of the invention. Other comonomers that may also be incorporated into the interpolymer include alkylacrylates, and alkylmethacrylates, especially the methyl, ethyl, butyl and 2-ethylhexyl esters. Maleate and fumarate esters, other vinyl and allyl esters and propene are also possible.

The key ingredient of the binder compositions which substantially contributes to the requisite hydrophobicity of the bonded web of fibers and substantially imparts the desired rewet characteristic is the anionic immobilizable surfactant system, preferably a phosphate ester surfactant or a sulfoalkanedioic acid half-ester surfactant. Other anionic surfactants such as sulfate and sulfonate surfactants do not work.

Phosphate ester surfactants, which are preferably in the form of their fugitive base salt for practicing the invention, include complex organic phosphate esters, complex organic polyphosphoric ester acid anhydrides, phosphate esters of complex aliphatic or aromatic hydroxyl compounds, phosphate esters of long chain linear and branched alcohols and alcohol ethers, such as phosphate esters of isooctyl, 2-ethylhexyl, cetyl, oleyl, and tridecyl alcohols, phosphated fatty glycols and glycol esters, phosphated mono- and diglycerides, mono- and dialkyl and alkyl aryl phosphate esters, phosphated polyether alcohols, such as poly(oxyethylene) phosphates, mono- and dialkyl and alkyl aryl poly(oxyethylene) acid phosphates, such as phosphated nonylphenoxyethanol. These phosphate ester surfactants are commercially available materials.

Preferred are the phosphate monoesters of alkyl or alkylaryl poly(oxyethylene) ethanols of the following general formula:

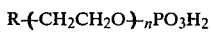

and the phosphate diesters of alkyl or alkylaryl poly(oxyethylene) ethanols of the following general formula:

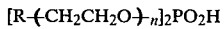

wherein R is the residue of a fatty alcohol, acid, amide or amine having from 10 to 18 carbon atoms, phenol, or an alkylphenol having from 10 to 18 carbon atoms and n is an integer from 0 to 100, but preferably greater than one and less than 15. Some specific examples of poly(oxyethylene) phosphates which can be used include the phosphate mono- and diesters of cetyl, oleyl, lauryl and, preferably, tridecyl poly(oxyethylene) ethanol ethers and the phosphate mono- and diesters of octyl and nonylphenyl poly(oxyethylene)ethanol ethers.

With regard to commercial polyethoxylate phosphate ester surfactants, such surfactants are typically mixtures of diester, monoester and the nonionic residue, frequently in a 55:35:10 or similar blend. Furthermore, it is believed that the diester readily hydrolyzes to the monoester plus the nonionic residue under polymerization or curing conditions. Because this effectively adds a nonionic polyethoxy ethanol containing surfactant, which demonstrates poor rewet properties, to the binder composition, it is desirable to minimize surfactant use and employ polyethoxylate phosphate esters with the shortest polyethoxylate chain, i.e. smallest value of n, consistent with emulsion stability. Such short polyethoxylate chain nonionics are believed to degrade the rewet characteristics of the nonwoven less than long chain polyethoxylate analogs which are more hydrophilic. Accordingly, monophosphate ester surfactants or short chain diester containing mixtures are preferred.

Nonwoven materials made using a binder composition containing a commercial polyethoxylate phosphate ester surfactant in which n ranges from about 3 to 10 show good low rewet. When n is less than about 3, the binder emulsion compositions generally possess inadequate stability. When n is greater than about 10, low rewet properties diminish. Binder compositions containing phosphate ester surfactants having about 4 or 5 ethoxyl groups are preferred because they do not require an acidic catalyst such as ammonium chloride for the curing step in order to produce a bonded nonwoven having good low rewet while still producing emulsions having usably low accelerated sedimentation and grits.

It is also speculated that polyethoxylate phosphate ester surfactants may become grafted into the polymer particles during polymerization and may not "wash off" during the initial strikethrough as occurs with the prior art post-added strikethrough surfactants. As evidence of this speculation, when emulsions are treated with ion exchange resin to convert the emulsions to the hydrogen form and remove aqueous phase surfactants, and then are titrated with base, the phosphate ester surfactant containing products exhibit weak acid levels which are too great for the acrylic acid levels charged, but are compatible with acrylic acid plus bound phosphate ester.

The free carboxylic acid group containing surfactants useful in the invention include, for example, the fatty acids; carboxylated alkyl polyesters; carboxylated fatty alcohols, such as tridecyl ether carboxylic acid; sulfoalkanoic acids and sulfoalkanedioic acid half-esters.

Representative of sulfoalkanedioic acids, the half-esters of which are useful for practicing the invention, are sulfomalonic acid, sulfosuccinic acid, sulfoglutaric acid, sulfoadipic acid, sulfopimelic acid, sulfosuberic acid, sulfoazelaic acid and sulfosebacic acid. Preferred are the sulfoglutarate, sulfoadipate, sulfomalonate and sulfosuccinate half-esters. Sulfosuccinate half-esters are most desirable for practicing the invention and are generally available commercially as the alkali metal salt.

Suitable sulfoalkanedioic acid half-esters useful in the practice of the invention can be represented by the following formula:

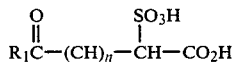

wherein $R_1$ is the residue of a fatty alcohol or amine or ethoxylated fatty alcohol or amine having from 10 to 18 carbon atoms and n is an integer from 0 to 10. The sulfoalkanedioic acid half-ester may exist as the free acid as shown in the above formula or as the mono- or disalt. However, when the surfactant is added, the counter ion of the carboxylic acid function is preferably a fugitive base. For the purposes of this invention, a half-ester is meant to include the amide functionality when $R_1$ is an amine as well as the ester functionality when $R_1$ is an alcohol with the latter preferred. Representative $R_1$ substituents are long chain linear or branched alcohols such as oleic, lauryl, decyl, isodecyl, undecylenyl, ricinoleic alcohols, ethoxylated alcohols, particularly ethoxylated fatty alcohols, such as ethoxylated lauryl alcohol, ethoxylated decyl alcohol and ethoxylated lanolin alcohol; ethoxylated alkylphenols, such as nonylphenol ethoxylate; alkanolamide, such as monooleamide and monococamide; and ethoxylated alkylamides, such as monooleamido-PEG-2.

Specific examples of sulfoalkanedioic acid half-esters include decyl sulfoadipate half-ester, monooleamide sulfosuccinate, tridecyl sulfoglutarate half-ester, polyethoxylol sulfosuccinate half-ester, nonylphenylpolyethoxylol sulfosuccinate half-ester, oleylpolyethoxylol sulfomalonate half-ester and the like.

Generally, the amount of anionic immobilizable surfactant, such as a phosphate ester or sulfoalkanedioic acid half-ester surfactant, which is added either before, during or after the polymerization reaction, is about 0.5 to 6 wt % based on emulsion solids, preferably 3 to 5 wt %. Preferably, for example, about 1 wt % of the anionic immobilizable surfactant is present during the polymerization reaction and about 2-4 wt % post-added.

While the sulfosuccinate half-esters give good rewet, the phosphate esters give slightly better tensile strengths, are lower in cost and, accordingly, are the preferred anionic immobilizable surfactant for use in the invention.

An important ingredient that must be added to the above described nonwoven binder composition; i.e., the vinyl acetate-ethylene-olefinically unsaturated carboxylic acid interpolymer emulsion containing an anionic immobilizable surfactant, is a crosslinking agent for the olefinically unsaturated carboxylic acid. Suitable crosslinking agents are polyvalent metal complex compounds which are added at levels from 0.2 to 5.0 wt % metal oxide equivalent based on emulsion solids. Exemplary of the polyvalent metal ion in the complex compounds are zinc, titanium, calcium, magnesium, vanadium, aluminum, zirconium and the like. Advantageously, the aluminum or zirconium metal ion is used to effect the crosslinking with the zirconium metal ion being the most preferred.

The polyvalent metal complex compounds comprise a polyvalent metal ion and counter ions or ligands which are sufficiently coordinated or associated with the central polyvalent metal ion so as to hinder interaction at room temperature between the anionic groups of the surfactant and interpolymer and the metal ion. However, at the elevated temperatures prevailing during the drying and cure of the binder composition these counter ions or ligands must be capable of being driven off or replaced by the anionic group of the surfactant or carboxylate group of the interpolymer so that polyvalent metal ion-surfactant or interpolymer interaction occurs. These counter ions or ligands may be, for example, volatile materials, such as, volatile carboxylic acids or amines. Examples of such counter ions or ligands are acetate, ammonia, methylamine, pyridine and the like. Suitable polyvalent metal complex compounds include ammonium zirconium carbonate, aluminum basic acetate and some of those metal complex compounds listed in U.S. Pat. No. 4,084,033 which is incorporated by reference.

In general, the binder compositions can be prepared in the following manner. Sufficient water is used in the emulsion polymerization to give a final solids in the range of 40 to 60%, preferably 50 to 55%. The vinyl acetate and ethylene are copolymerized in the presence of the olefinically unsaturated carboxylic acid in the aqueous medium under ethylene pressures not exceeding about 100 atmospheres in the presence of a catalyst and an emulsifying agent which preferably comprises an anionic immobilizable surfactant. The vinyl acetate can be added over a period of time during the polymerization (delay addition) or, preferably, is all present at the beginning (batch addition). When reference is made to "delay additions", incremental additions which are uniform both with respect to quantity and time are contemplated.

The olefinically unsaturated carboxylic acid is added neat or in an aqueous solution, preferably as a delay addition. The pH of the carboxylic acid monomer delay should not be adjusted higher than about 4, desirably not higher than about 3.3, by using a fugitive base, preferably ammonia, if good low rewet properties of the emulsion are to be maintained. In other words, the carboxylic acid monomer, such as acrylic acid, should be added unneutralized or preferably at a pH of about 2.5 to 3.3.

Ethylene is added batch wise at a pressure from about 20 to 55 atmospheres. The ethylene pressure is adjusted to give the desired polymer glass transition temperature. When the free monomers are reduced to about a 1 to 2% level, the reaction is transferred to a degasser and finished, by the addition of more catalyst, to less than 0.2% free monomer.

Various free-radical forming catalysts can be used in carrying out the polymerization of the monomers. Combination type catalysts employing both reducing agents and oxidizing agents can also be used and are generally referred to as a redox system. The reducing agent is often referred to as an activator and the oxidizing agent as an initiator. Suitable reducing agents or activators include bisulfites, sulfoxylates, or other compounds having reducing properties such as ferrous salts, ascorbic and erythorbic acids, and tertiary aromatic amines. The oxidizing agents or initiators include hydrogen peroxide, organic peroxides such as benzoyl peroxide, t-butyl hydroperoxide and the like, persulfates, such as ammonium or potassium persulfate, perborates, and the like. Specific combination type catalysts or redox systems which can be used include hydrogen peroxide and zinc formaldehyde sulfoxylate; hydrogen peroxide, ammonium persulfate, or potassium persulfate, with sodium metabisulfate, sodium bisulfite, ferrous sulfate, dimethylaniline, zinc formaldehyde sulfoxylate or sodium formaldehyde sulfoxylate. Other types of catalysts that are well known in the art can also be used to polymerize the monomers.

It is preferred, however, to use a binder composition which is not a source of free formaldehyde since the bonded nonwovens will contact human skin. Accordingly, a ketone bisulfite/peroxide redox initiator system is used to eliminate formaldehyde containing components and to give a formaldehyde free binder having good properties on a polyester web for a nonwoven application in diaper top sheets. Preferably, the formaldehyde free redox initiator system comprises acetone bisulfite and t-butyl hydroperoxide (TBHP). The acetone bisulfite activator should be used in substantial molar excess over the TBHP, for example from 2:1 to 10:1, most preferably 4 to 6:1. The instantaneous molar addition rate of the acetone bisulfite should also always be in excess of the TBHP addition rate to maintain the reaction. Advantageously, a mixture of bisulfite and TBHP is used in the finishing step for reducing the free monomer content to less than 0.2%.

The reaction can be run at any temperature from sub-ambient to 90° C., but most preferably is maintained at about 40° to 60° C. The premix should be adjusted to give an average running pH in the range of about 4.0 to 6 using buffers, preferably buffers comprising a fugitive base salt as a source of fugitive base for the phosphate ester surfactant, as is well known in the art. The total reaction time is about 3.5 to 6 hours depending largely upon the heat removal capacity of the reactor unit.

The catalyst is employed in an amount of 0.1 to 2%, preferably 0.25 to 0.75% based on the weight of vinyl acetate introduced into the system. The activator is ordinarily added in aqueous solution in an amount generally 4 to 6 times the amount of catalyst.

Emulsifying agents in addition to the anionic immobilizable surfactant can be added to the polymerization recipe. Suitable emulsifying agents include nonionic and anionic agents disclosed in U.S. Pat. No. 3,922,462 which is incorporated by reference.

Another method for producing vinyl acetate-ethylene containing copolymers which is useful for preparing the interpolymer emulsions of the instant binder compositions comprises first forming an aqueous emulsion of vinyl acetate and stabilizer and charging this emulsion to a reactor. The reactor is pressurized with ethylene to an ethylene-equilibrium pressure of about 200 to 500 psig (13.6 to 34 atm). The resulting reaction mixture is adjusted to a temperature from about 10° to 30° C. Polymerization is initiated by the addition of a catalyst at a rate such that the reaction mixture is brought to a temperature of from 45° to 85° C., preferably 50° to 60° C., within a period of one hour or less, preferably 30 minutes. The polymerization is continued until the vinyl acetate content is reduced below about 0.2 wt % of the copolymer.

In order to effectively use the vinyl acetate-ethylene-olefinically unsaturated carboxylic acid binder emulsion to prepare nonwoven fabrics, the emulsion, which may be diluted to any desired level with water, is treated with a polyvalent metal complex compound as a crosslinking agent. Useful crosslinking agents are the polyvalent metal ions, preferably the zirconium and aluminum ions. Zirconium can be added as the ammonium zirconium carbonate or as the acetate complex. Desirably, ammonium zirconium carbonate (AZC) is added at levels from about 0.2 to 3.6% AZC (as zirconium dioxide solids on emulsion solids); most preferably at levels of 0.4 to 0.8%. A small amount, for example 0.5 to 1%, of acidic catalyst, such as ammonium chloride, is optionally added, especially when the binder composition contains a high polyethoxylated phosphate ester. Aluminum is preferably added as aluminum basic acetate $[Al_2O(OAc)_4 \cdot XH_2O]$ at about 0.4 to 2.5%, preferably at about 1.4% solids on emulsion solids.

Without being held to any particular theory, it is believed that complex formation involving a phosphate ester surfactant and a polyvalent metal ion, for example zirconium, may be shown as follows:

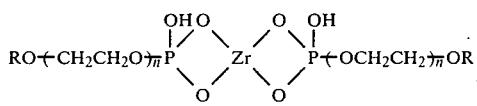

and that involving a sulfosuccinate half-ester surfactant may be shown as follows:

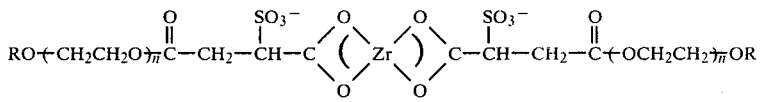

The metal ion also reacts with the carboxylic acid groups of the interpolymer in a manner like that shown for the sulfosuccinate half-ester. It is believed that this interaction of the surfactant, polyvalent metal ion and the carboxylic acid functionality of the interpolymer is greatly responsible for the good wet tensile strength and surprising low rewet properties of the nonwoven product.

The necessity for an acidic catalyst such as ammonium chloride with high polyethoxylated phosphate ester surfactants but with low polyethoxylated analogs is believed attributable to a partition in the insolubilization of zirconium. During cure zirconium can form species rich in zirconium oxides (low crosslinking efficiency) or rich in coordinated carboxylates and phosphates (high crosslinking efficiency). The presence of an acidic catalyst should slow oxide formation and, presumably, allow more time for phosphate and/or carboxylate diffusion and complex formation with the zirconium ion. The low polyethoxylate analogs, when uncomplexed, contribute less rewet degrading nonionic polyethoxylate units ($-CH_2CH_2O-$) than the high polyethoxylate analogs, and thus require less efficient complexation. Having shorter chains, they also graft and become permanently bound to the polymer less readily and, being lower in molecular weight, contribute more acid in and of themselves than high polyethoxylate analogs.

Preadjustment of the binder emulsion pH to less than about 7, for example pH 5.5 to 7.0, preferably pH 6.5 to 7, several days before coating is frequently beneficial in increasing the cure rate. The pH adjustment must be done carefully using dilute aqueous solutions of ammonium hydroxide.

An acid catalyst may be optionally included in the aqueous binder emulsion composition at the time it is applied to the fibrous web or the acid catalyst may be applied to the fibrous web before or after the interpolymer is applied. Examples of acidic catalysts that may be used include mineral acids, such as hydrogen chloride, organic acids, such as oxalic acid, dichloroacetic acid, and p-toluene sulfonic acid, and acidic salts such as ammonium sulfate or chloride. The amount of catalyst is generally about 0.5 to 2% of the total resin.

The above described vinyl acetate-ethylene-olefinically unsaturated carboxylic acid interpolymer binder emulsions containing an anionic immobilizable surfactant and a polyvalent metal complex compound is used to prepare nonwoven fabrics by a variety of methods known in the art which, in general, involve the impregnation of a loosely assembled mass of fibers with the binder composition, followed by moderate heating to dry the mass. In the case of the present invention, this moderate heating also serves to cure the binder by forming a crosslinked interpolymer. The heating "destabilizes" the counter ions or ligands surrounding the central polyvalent metal ion either driving them off if they are volatile or effecting a replacement by the anionic group of the surfactant and the interpolymer.

The starting layer or mass can be formed by any one of the conventional dry or wet techniques for depositing or arranging fibers in a web or layer. These techniques include carding, garnetting, air laying and the like. Typically, the fibers extend in a plurality of diverse directions in general alignment with the major plane of the fabric, overlapping, intersecting and supporting one another to form an open, porous structure. Examples of fibers that can be used are the natural cellulose fibers such as cotton and hemp and the synthetic cellulose fibers such as rayon and regenerated cellulose; natural fibers such as wool or jute; artificial fibers such as cellulose acetate; synthetic fibers such as polyamides, nylon, polyesters, acrylics, polyolefins, i.e., polyethylene, polyvinyl chloride, polyurethane, and the like, alone or in combination with one another. Polyester fibers are preferred for the preparation of nonwoven disposable diaper innerliners.

The fibrous starting layer is subjected to at least one of the several types of bonding operations to anchor the individual fibers together to form a self-sustaining web. Some of the better known methods of bonding are overall impregnation, spraying or printing the web with intermittent or continuous straight or wavy lines or areas of binder extending generally transversely or diagonally across the web and additionally, if desired, along the web. In general, diaper innerliners are prepared by overall impregnation or saturation of the fibrous web with the binder composition.

The amount of binder, calculated on a dry basis, applied to the fibrous starting web suitably ranges from about 10 to about 100% or more by weight of the starting web, and preferably from about 10 to about 60% by weight of the starting web. The impregnated web is then dried and cured by methods common to the art. Various time-temperature relationships for drying and curing can be employed as are well known in the art, shorter times at higher temperatures or longer times at lower temperatures being used.

The following examples are provided to illustrate the invention and are not intended to restrict the scope thereof:

EXAMPLE 1

The preparation of various vinyl acetate-ethylene-alpha,beta unsaturated carboxylic acid interpolymer binder emulsion systems (Runs 1 to 30) was carried out in a 15 gallon stirred, stainless steel reaction vessel equipped with a jacket, the agitation system involving two turbine blades.

In preparing the binder emulsion of Run 16, the following charge was introduced into the pressure reaction vessel:

Premix:

-continued

| | |
|---|---|
| Dextrol OC-20 (phosphate ester of ethoxylated nonylphenol) | 810 gm (3%) |
| FeSO$_4$.7H$_2$O | 2 gm |
| Deionized (DI) H$_2$O | 19.07 kg |
| Activator (see delay solution below) | 225 gm |
| Sodium Acetate | 30 gm in 100 ml H$_2$O |
| The pH was adjusted to 4.2 with 55 gm of NH$_4$OH | |
| Monomer: | |
| Vinyl acetate | 21.6 kg |

The reactor was pressurized with ethylene to 500 psig (35 atm) at 30° C. and heated to 50° C. Agitation was 225 rpm.

The following delay solutions were prepared:

| | | |
|---|---|---|
| Activator | Sodium bisulfite (Na$_2$S$_2$O$_5$) | 258 gm |
| | Acetone | 158 gm |
| | DI H$_2$O | 6045 gm |
| Delay Rate | 1350 ml/hr | |
| Catalyst | t-Butyl hydroperoxide (70%) | 154 gm |
| | DI H$_2$O | 3.45 kg |
| Delay Rate | Demand Addition | |
| Comonomer | Acrylic Acid | 1854 gm |
| | DI H$_2$O | 2.78 kg |
| | Adjust to pH 2.5 with 30 g NH$_4$OH | |
| Delay Rate | 2070 gm in 1 hr. | |

The reaction was initiated by starting the catalyst and activator delays. After an exotherm was obtained, catalyst was switched to demand control to maintain reaction temperature and the acrylic acid delay started. Reactor temperature was maintained at 46°-50° C. and the jacket in the range of 20°-40° C. to reduce the vinyl acetate monomer to 1.5% in four hours. T-butyl hydroperoxide (TBHP) consumption was 30.1 gm, acetone bisulfite consumption was 322 gm. The batch was transferred to a degasser and treated with 37.5 gm Na$_2$S$_2$O$_5$ in 150 ml H$_2$O. TBHP, 300 ml of a 7.2% solution, was pumped in over a 0.5 hour period to reduce the vinyl acetate monomer level below 0.5%. The product showed a Tg of −7° C. and had good performance properties as a nonwoven binder when formulated with a crosslinking agent and padded onto a web of polyester fibers as described below.

Runs 1 through 15 and 17 through 30 were conducted in a manner similar to the above described Run 16. The amount of vinyl acetate monomer and the ethylene pressure was the same as in Run 16 and the amount of Dextrol OC-20 surfactant and acrylic acid monomer were as indicated in Table 1. The acrylic acid delay solution was added within the time period shown in Table 1 with adjustment of the pH of the acrylic acid solution with ammonium hydroxide as indicated.

Padding Testing Samples

The base stock used for padding was lightly-bonded rando polyester having a nominal base weight of approximately 0.7 oz/yd$^2$ (23.7 g/m$^2$). In preparation for padding, the polyester was cut as follows:

4 in [10.2 cm (CMD)]×9 in [22.9 cm (MD)] for tensiles
4 in [10.2 cm (CMD)]×12 in [30.5 cm (MD)] for reabsorbency The initial weight of each sample was recorded to 0.1 mg.

Padding formulations were made up at approximately 17% solids for a 50% binder add-on to polyester. Each polyester sample was individually saturated with the formulation, then fed through the pressing rolls of an Atlas laboratory wringer with a 105 g arm load to squeeze excess formulation from the sheet.

After padding, samples were placed in a 300° F. (149° C.) air circulating oven for 5 and 15 minutes. All samples were conditioned overnight in a constant temperature and humidity room [70° F. (21° C.), 50% RH], then final weights were obtained and % binder add-on was calculated.

$$\frac{\text{Final Wt.} - \text{Initial Wt.}}{\text{Initial Wt.}} \times 100 = \% \text{ Binder Add-on}$$

Samples with 50±3% binder add-on were used for evaluation of dry and wet tensile strengths and adsorption/readsorption. For Runs 1–30 the padding formulations contained 0.8% ammonium zirconium carbonate and 0.7% ammonium chloride.

Tensiles

Padded polyester samples measuring 4 in [10.2 cm (CMD)]×9 in [22.9 cm (MD)] were die cut 0.5 in (MD)×4 in [10.2 cm (CMD)] for tensile testing. A minimum of eight tensiles were cut; four for dry tensiles and four for wet.

An Instron tester, model # TM or 1122 was set for polyester tensiles as follows:
Load Cell: B
Pneumatic grips
Jaw Span: 2 in (5.1 cm)
Chart and Crosshead Speed: 5 in/min (12.7 cm/min)

Dry tensile strips were pulled individually. Wet tensile strips were brushed once on each side with 0.5% Aerosol OT surfactant solution, then pulled immediately.

Tensile strength at break in grams for each sample were doubled, then results were averaged to obtain the mean ±2 standard deviations. Final results were expressed in grams/linear inch (gli) and % elongation.

Absorption/Reabsorption Test (ART)

4000 cc beaker filled with deionized water was placed into a water bath maintained at 80° F. (27° C.) and allowed to equilibrate.

Padded polyester samples which were treated at 300° F. (149° C.) for 5 minutes were cut approximately 4 in×12 in (10.2 cm×30.5 cm) such that each sample weighed about 1.0 g. The sample was rolled and placed in a 3.0 g wire basket. The wire basket had a diameter of approximately 1.5 in, a height of 3 in (7.6 cm), and was sealed at one end.

The sample was dropped on its side into the beaker from a height of one inch (2.5 cm). The time for the sample to sink was recorded as a measure of rate of water absorption. If the sample did not sink within 10 minutes, the test was discontinued and the sink time was recorded as >10 minutes.

The sample was submerged, removed and hung to dry for one hour in the constant temperature and humidity room. The test was then repeated as above two more times to determine reabsorption unless the first two sink times were greater than 10 minutes.

This test was designed to afford a means for determining, in an approximate manner, the rewet properties of a bonded nonwoven fabric sample. The first sink test (absorption) does not directly correspond to measurement of the strikethrough property of the nonwoven fabric because of the absence of any added strikethrough surfactant to facilitate the passage of water as is customary in the commercial art. The second and third testing more closely correspond to the rewet property since the first test would simulate removal of the strikethrough surfactant as occurs in actual use.

Table 1 also shows the results of the Tensiles and Absorption/Reabsorption Tests. Although most of the Runs demonstrated an absorption (strikethrough) time of 10 minutes or more, the strikethrough of actual commercial nonwoven materials would be greatly improved to acceptable levels by the customary addition of strikethrough surfactants. To a large degree, reabsorption times were nearly 10 minutes or longer for the runs, specifically Runs 1-16, 20-25, 27, 28 and 30. Sink times of several minutes are considered indicative of good low rewet properties (hydrophobicity). Sink times of ten minutes or more are exceptionally good.

Runs 17-19, and to a lesser extent Runs 22-25, gave relatively shorter sink times indicating the deleterious effect of a high pH of the acrylic acid delay, i.e. greater than about pH 4. Runs 12, 14, 16, 20, 21, 27 and 28, in which the acrylic acid delay had a pH in the range of 2.5 to 3.3, showed reabsorption times of greater than 10 minutes.

In Run 26, the premix containing the phosphate ester surfactant was adjusted with aqueous sodium hydroxide instead of ammonium hydroxide. The bonded nonwoven sample of Run 26 had shorter sink times than the samples of comparable Runs 8, 9, 13 and 15 which were adjusted with ammonium hydroxide. The fugitive base salt of the phosphate ester surfactant gave superior results.

Run 29 demonstrated increasingly shorter sink times as did a control sample tested at the same time. This might have resulted from inadequate cure.

The dry and wet tensile strengths of samples cured for 5 and 15 minutes and expressed in grams per linear inch (gli) are also provided in Table 1. All the Runs provided bonded nonwoven polyester fiber webs having acceptable tensiles.

TABLE 1

| Run | Surfactant Level % | Acrylic Acid Level % | Acrylic Acid Delay Time Hours | pH of Acrylic Acid (if adjusted) | Total Reaction Time Hours | Tg | Final pH | Average Running pH | Total T—BHP Consumption | Total Activator Consumption | Dry Tensiles 5/15 Min @ 300° F. g/i | Wet Tensiles 5/15 Min @ 300° F. g/i | Absorption/ Reabsorption Test |
|---|---|---|---|---|---|---|---|---|---|---|---|---|---|
| 1 | 3.6 | 3.0 | 2.5 | | 3.0 | −2 | — | 5.24 | 61.6 | 257 | 2468/2938 | 2120/2404 | >10, 10, >10 |
| 2 | 3.6 | 3.0 | 2.5 | | 3.0 | −3.5 | — | 4.83 | 42.9 | 251 | 3392/2828 | 2672/2262 | >10, >10 |
| 3 | 5.0 | 3.0 | 2.5 | | 3.0 | 1.5 | — | 4.8 | 33.7 | 240 | 3132/2486 | 2680/2202 | >10, >10 |
| 4 | 6.0 | 2.0 | 3.75 | | 4.0 | −1 | 4.52 | 4.9 | 30.4 | 182 | 2300/2680 | 1881/2300 | >10, >10 |
| 5 | 5.0 | 3.0 | 2.5 | | 3.0 | 0.5 | — | 4.57 | 30.1 | 280 | | | |
| 6 | 5.0 | 3.0 | 2.5 | | 3.75 | 0 | — | 5.34 | 25.6 | 337 | 3140/3049 | 2761/2414 | 5, >10, >10 |
| 7 | 5.0 | 3.0 | 1.75 | | 5.5 | −10.0 | — | 5.45 | 26.5 | 280 | 3131/2845 | 2623/2387 | 7, >10, >10 |
| 8 | 5.0 | 3.0 | 1.75 | | 4.0 | −7.5 | — | 5.40 | 31.2 | 307 | 3460/3330 | 3170/2680 | >10, >10 |
| 9 | 5.0 | 3.0 | 1.75 | | 4.0 | −8.5 | — | 5.76 | 30.7 | 310 | 2597/2393 | 2257/2354 | 8, >10 |
| 10 | 5.0 | 3.0 | 1.75 | Acetic | 4.0 | −8 | — | 4.62 | 29.0 | 330 | 2799/2754 | 2469/2457 | >10, >10 |
| 11 | 5.0 | 3.0 | 1.75 | H₂SO₄ | 4.25 | −5.5 | — | 4.11 | 26.5 | 307 | | | |
| 12 | 4.0 | 3.0 | 2.00 | 3.3 | 4.25 | −6.5 | — | 5.77 | 21.2 | 333 | 3030/3000 | 2670/2840 | >10 >10 |
| 13 | 5.0 | 3.0 | 1.75 | | 4.25 | −5 | — | 5.20 | 26.5 | 345 | 3060/2870 | 2690/2450 | 5, >10, >10 |
| 14 | 5.0 | 3.0 | 1.00 | 2.5 | 3.50 | −7.5 | — | 5.40 | 39.0 | 312 | 3490/2130 | 3200/2490 | >10, >10 |
| 15 | 5.0 | 3.0 | 1.75 | | 4.10 | −3 | — | 5.37 | 21.7 | 347 | 3090/2725 | 2460/2415 | >10, >10 |
| 16 | 3.0 | 3.0 | 1.00 | 2.5 | 3.75 | −7 | — | 4.73 | 30.1 | 322 | 3090/3560 | 2540/3100 | >10, >10 |
| 17 | 5.0 | 3.0 | 1.00 | 4.1 | 4.25 | −2.5 | — | 5.79 | 27.6 | 338 | 3010/3300 | 2690/2800 | 2 1, 5 |
| 18 | 4.0 | 3.0 | 1.00 | 4.1 | 3.75 | −3.5 | — | 5.23 | 31.5 | 345 | 2902/3160 | 2170/2390 | 2 1, 2 |
| 19 | 3.0 | 3.0 | 1.00 | 4.1 | 4.25 | −6.0 | — | 5.69 | 34.8 | 336 | 2970/3280 | 2220/2610 | 2 1, 7 |
| 20 | 3.0 | 3.0 | 3.0 | 2.5 | 4.00 | −1.5 | — | 5.27 | 28.7 | 343 | 3740/2890 | 3000/2710 | >10 >10, >10 |
| 21 | 3.0 | 3.0 | 3.0 | 2.5 | 4.00 | −3.5 | — | 5.52 | 23.1 | 340 | 2900/3510 | 2370/2850 | >10 >10, >10 |
| 22 | 5.0 | 3.0 | 3.0 | 4.1 | 4.25 | −3.5 | 6.04 | 6.05 | 34.0 | 340 | 2670/2820 | 2120/2360 | 6, 3, >10 |
| 23 | 3.0 | 3.0 | 3.0 | 4.1 | 4.0 | −5.5 | 5.85 | 6.00 | 36.2 | 332 | 2990/2920 | 2180/2440 | 5 6, >10 |
| 24 | 3.0 | 3.0 | 3.0 | 4.1 | 4.5 | −3.0 | 5.98 | 6.10 | 24.8 | 254 | 2950/3080 | 2290/2510 | 4 >10, 8 |
| 25 | 3.0 | 3.0 | 1.75 | 4.1 | 4.15 | | 5.74 | 5.78 | 34.3 | 173 | 2950/2830 | 2550/2300 | 7 10, 10 |
| 26 | 5.0 | 3.0 | 1.75 | — | 4.0 | | 5.30 | 5.19 | 27.9 | 339 | 2935/2565 | 2215/1925 | 4, 3, 9 |
| 27 | 3.0 | 3.0 | 1.75 | 3.0 | 4.0 | | 5.75 | 5.69 | 25.4 | 349 | 2830/2695 | 2215/2165 | 9, >10, >10 |
| 28 | 4.0 | 3.0 | 1.75 | 3.3 | 4.0 | | 5.70 | 5.58 | 22.6 | 345 | 3030/3135 | 2475/2415 | 7, >10, >10 |
| 29 | 5.0 | 3.0 | 1.75 | — | 4.75 | | 5.60 | 5.40 | 20.6 | 340 | 2820/2680 | 2340/2380 | 8, 3, 0.5 |
| 30 | 4.5 | 3.0 | 1.75 | — | 5.10 | | — | 5.41 | 22.3 | 429 | 2715/2870 | 2205/2295 | 10, >10, >10 |

EXAMPLE 2

Runs 31 through 48 were performed following a procedure similar to that used for the preparation of the Runs described in Example 1. Whereas the same phosphate ester surfactant was used throughout the runs of Example 1, the runs of this Example used various surfactants and surfactant combinations as indicated in Table 2. Table 3 further identifies the surfactants listed in Table 2. Runs 44 and 45 yielded extremely viscous emulsions which coagulated.

While most of the Runs incorporated about 3% of acrylic acid (AA), Runs 32, 33, and 45–48 used crotonic acid (CA) at the indicated levels. The test samples of polyester fiber webs were again bonded with the binder emulsions containing 0.8% ammonium zirconium carbonate and from 0.8 to 1% ammonium chloride with curing effected at 300° F. (149° C.) for 5 and 15 minutes. Five minute cured samples were used for the Absorption/Reabsorption Test.

From Table 2, which also includes Runs 6, 7 and 12, it can be seen that Runs 31, 32, 34, 37 and 40 contained surfactants other than a phosphate ester or sulfosuccinate half-ester surfactant. With exception of Run 32 and the third testing of Run 37, these Runs showed very short sink times and, accordingly, inferior rewet properties. The surfactants used in Runs 31, 32, 34, 37 and 40 were nonionic materials or anionic sulfate or sulfonate materials.

A phosphate ester surfactant was used without any other surfactant in Runs 7, 12, 21, 35 and 41–43 and the resultant bonded nonwoven samples with the exception of Run 41 showed good or exceptional low rewet properties. Runs 6, 38, 39 and 46 contained a phosphate ester surfactant in combination with either a nonionic surfactant or an anionic sulfate or sulfonate surfactant. Having the phosphate ester surfactant in these combination surfactant runs at a level of at least 2.5% afforded good rewet properties as shown by Runs 6 and 38. Relatively poorer rewet properties were obtained for Runs 39 and 46 in which the phosphate ester was present at 1.5% and 1.1% levels, respectively, although both Runs demonstrated a 10-minute sink time on the third testing of the sample.

The sulfosuccinate half-ester containing Runs 33, 36, 47 and 48 showed, in general, exceptional rewet properties. The sulfosuccinate half-ester surfactants were added to the premix as the alkali salt and the pH was adjusted to about 3 with sulfuric acid.

The wet tensiles for all the Runs were comparably acceptable excepting Run 46 which showed unusually low values.

TABLE 2

| Run | Surfactant* | Comonomer | Wet Tensile | Absorption/Reabsorption Test |
|---|---|---|---|---|
| 6 | 5% OC-20, 1% CO-430 | 3% AA | 2761/2414 | 4, >10 |
| 7 | 5% OC-20 | 3% AA | 2623/2387 | 7, >10 |
| 12 | 4% OC-20 | 3% AA | 2670/2840 | >10 >10 |
| 21 | 3% OC-20 | 3% AA | 2370/2850 | >10 >10 |
| 31 | 3% CO-436/0.5% SVS | 3% AA | 2370/2850 | 0.3 0.5 |
| 32 | Nonionic Mix** | 3.8% CA | 2200/2690 | 4, >10 |
| 33 | 3% A-102 | 3.8% CA | 2230/2500 | >10 >10 |
| 34 | 3% DS-4 | 3% AA | 2790/2910 | 0.1, 0.1 |
| 35 | 3.75% QS-44 | 3% AA | 2650/2520 | >10 >10 |
| 36 | 3% A-103 | 3% AA | 2230/2320 | >10 2, >10 |
| 37 | 2% CO-433/1% CO-430 | 3% AA | 1990/2330 | 0.1 0.2, >10 |
| 38 | 2.5% OC-20/.75% DS-4 | 3% AA | 2360/2490 | >10 >10 |
| 39 | 1.5% OC-20/1.5% CO-433 | 3% AA | 2000/2260 | 1.0 1.0, >10 |
| 40 | 3% A-246L | 3% AA | 2080/1950 | 0.03 0.03, 0.07 |
| 41 | 3% RS-710 | 3% AA | 2560/2200 | 1.0 0.30, 1 |
| 42 | 3% DS-10N | 3% AA | 2370/2780 | 5.0 4.0, >10 |
| 43 | 3% RS-410 | 3% AA | 2430/2880 | 8.0 9, >10 |
| 44 | 3% RS-610 | 3% AA | | Viscous, Failed |
| 45 | 3% OC-20, 0.5% SVS | 3.8% CA | | Thick, Failed |
| 46 | 1.1% OC-20, 0.5% 250 LR | 1.5% CA | 1240/1620 | 0.6 4, >10 |
| 47 | 3% A-102 | 3.8% CA | 2590/2670 | 6.4, >10 >10 |
| 48 | 3% A-102 | 1.9% CA | 2420/2700 | >10, >10 6.5 |

*See Table 3 for identification of the surfactants.
**Natrosol 250 GR, 1.1%; Igepal CO-630 and CO-880, 0.5% each; Pluronics F-68 and L-64, 0.5% each.

TABLE 3

| | |
|---|---|
| OC-20 | Dextrol OC-20, Dexter Chemical Corp. - anionic surfactant - complex organic phosphate of polyethoxylated (9-10 units) nonylphenol, a mixture of mono- and diester. |
| CO-430 | Igepal CO-430, GAF Corp - nonionic surfactant - nonylphenoxypoly(ethyleneoxy) ethanol. |
| CO-433 | Alipal CO-433, GAF Corp. - anionic surfactant - sodium salt of sulfated nonylphenoxypoly (ethyleneoxy) ethanol. |
| CO-436 | Alipal CO-436, GAF Corp. - anionic surfactant - ammonium salt of sulfated nonylphenoxypoly (ethyleneoxy) ethanol. |
| SVS | Sodium vinyl sulfate, Air Products and Chemicals - anionic comonomer. |
| GR/LR 250 | Natrosol GR 250/LR 250, Hercules, Inc. - nonionic surfactant - carboxymethylcellulose. |
| CO-630/880 | Igepal CO-630 and 880, GAF Corp. - nonionic surfactants - nonylphenoxypoly(ethyleneoxy) ethanols. |
| F-68/L-64 | Pluronics F-68/L-64, BASF Wyandotte - nonionic surfactants - polyethoxylated condensate of propyleneoxide and propylene glycol. |
| A-102 | Aerosol A-102, American Cyanamide - anionic surfactant - disodium ethoxylate $C_{10}$–$C_{12}$ alcohol half ester of sulfosuccinic acid. |
| DS-4 | Siponate DS-4, Alcolac, Inc. - anionic surfactant - sodium dodecylbenzenesulfonate. |
| A-103 | Aerosol A-103, American Cyanamide - anionic surfactant - disodium ethoxylated nonylphenol half ester of sulfosuccinic acid. |
| QS-44 | Triton QS-44, Rohm and Haas Co. - anionic surfactant - complex organic phosphate ester, alkylphenol polyethoxyethanol based. |
| RS-710 | Gafac RS-710, GAF Corp. - anionic surfactant - organic phosphate ester of a polyethoxylated aliphatic alcohol. |
| RS-610 | Gafac RS-610, GAF Corp. - anionic surfactant - organic phosphate ester of a polyethoxylated aliphatic alcohol. |
| RS-410 | Gafac RS-410, GAF Corp. - anionic |

TABLE 3-continued surfactant.- organic phosphate ester of a
polyethoxylated aliphatic alcohol.

| | |
|---|---|
| DS-10N | Wayfos DS-10N, Philip A. Hunt Chemical Co. - anionic surfactant - complex organic phosphate ester of a polyethoxylated nonylphenol. |
| A-246L | Siponate A-246L, Alcolac, Inc. anionic surfactant - sodium alpha-olefinsulfonate. |

EXAMPLE 3

This example shows the need for a polyvalent metal ion as the crosslinking agent in the binder composition for good rewet properties.

Runs 49 through 57 were performed following a procedure similar to that used for the preparation of the Runs described in Example 1. While an alpha,beta unsaturated carboxylic acid, namely acrylic acid (AA) or crotonic acid (CA), was used in Runs 49–51, 53–54, and 56–57, Runs 52 and 55, which are representative of a prior art nonwoven binder composition, A-105 emulsion marketed by Air Products and Chemicals, Inc., used N-methylolacrylamide (NMA) as the crosslinkable functionality in the interpolymer in place of the carboxylic acid monomer.

The crosslinking agents used in this Example were ammonium zirconium carbonate [AZC], aluminum basic acetate [$Al_2O(Ac)_4$], tris(hydroxymethyl)aminomethane [TRIS], and a melamine/formaldehyde external crosslinker [Cymel 303]. Ammonium chloride [$NH_4Cl$] was used to crosslink the N-methylolacrylamide units as is customary in the art.

Runs 49–51, 53 and 54 contained 5% OC-20 phosphate ester surfactant and Runs 56 and 57 contained 4% OC-40 phosphate ester surfactant.

TABLE 4

| | | | Tensiles (gli) 5/15 min at 300° F. | | Absorption/Reabsorption |
|---|---|---|---|---|---|
| Run | Comonomer | Crosslinker | Dry | Wet | Test (min) |
| 49 | 3% AA | 0.8% AZC | 3220/3568 | 2570/2684 | 4.25, >10, >10# |
| 50 | 3% AA | 0.8% $Al_2O(Ac)_4$ | 2888/2874 | 2150/2760 | 4, 0.9, 8.5# |
| 51 | 3% AA | 1.6% $Al_2O(Ac)_4$ | 3200/2838 | 2550/2308 | 2.3, 2.3, 10# |
| 52 | 5% NMA | 1% $NH_4Cl$ | 2800/2690 | 2390/2480 | 0.6, 4.3, >10 |
| 53 | 3% AA | 0.8% AZC, 0.7% $NH_4Cl$ | 2960/3250 | 2490/2720 | >10, >10 |
| 54 | 3% AA | 1.8% TRIS | 2680/3000 | 1780/1860 | 0.05, 0.05, 0.08 |
| 55 | 5% NMA | 1% $NH_4Cl$ | 2875/2998 | 2523/2762 | 0.3, 0.3, 2.8 |
| 56 | 3% AA | 0.8% AZC, 0.7% $NH_4Cl$ | 2806/3606 | 2233/2976 | >10, >10, >10 |
| 57 | 3% AA | 5% Cymel 303, 1% $NH_4Cl$ | 2914/3107 | 2689/2952 | 0.1, 0.05, 0.8 |

15 min cure

From Table 4 it can be seen that aluminum basic acetate and melamine formaldehyde resins produced wet and dry tensiles comparable to the N-methylolacrylamide crosslinked or the ammonium zirconium carbonate crosslinked binder while the tensiles were inferior for the TRIS containing Runs. TRIS and the melamine formaldehyde resins gave exceptionally poor rewet indicating the need for a polyvalent metal ion in the composition. Aluminum, although not as good as zirconium in these runs, did improve rewet.

EXAMPLE 4

This example shows that a binder composition requires both the phosphate ester surfactant and zirconium ion crosslinker in order to afford a bonded nonwoven fabric sample having good low rewet properties.

Runs 58 through 68 were performed following a procedure similar to that used for the preparation of Runs described in Example 1, the unsaturated carboxylic acid comonomer being acrylic acid. Table 5 shows the surfactant, the number of oxyethylene units $(EO)_n$ in the phosphate ester surfactant and the crosslinker used in each run.

Runs 58, 61, 64 and 66 did not contain the polyvalent metal ion and their respective bonded nonwoven fabric samples possessed very poor rewet properties.

The data in Table 5 (Runs 59, 60, 62 and 63) also show that ammonium chloride catalyst is not required for the binder composition if the polyethoxylated phosphate ester surfactant contains about 3 to B 4 oxyethylene units.

TABLE 5

| Run | Surfactants** | Crosslinkers | Surfactant Backbone | $(EO)_n$ | Wet Tensile @ 300°, 5/15 min., gli | Absorption/Reabsorption Test (min) |
|---|---|---|---|---|---|---|
| 58 | 5% OC-20 | — | nonylphenol | 9–10 | 2250/2620 | <0.1, <0.1, 0.7 |
| 59 | " | 0.8% AZC | | | 2240/2810 | 5, 1, >10 |
| 60 | " | 0.8% AZC 1% $NH_4Cl$ | | | 2480/2480 | 6, >10, >10 |
| 61 | 3% OC-40 | — | tridecyl | 3–4 | 2680/2230 | <0.1, <0.1, <0.1 |
| 62 | " | 0.8% AZC | | | 2930/2880 | >10, 4, >10 |
| 63 | " | 0.8% AZC 1% $NH_4Cl$ | | | 2760/3040 | >10, >10, >10 |
| 64 | 3% RE-410 | — | nonylphenol | ~6 | 2360/2390 | 0.07, 0.03, 0.08 |
| 65 | " | 0.8% AZC 1% $NH_4Cl$ | | | 2300/2560 | >10, 2.0, >10 |
| 66 | 3% OC-20 | (0.1% TAC)* | nonylphenol | 9–10 | 2150/2080 | 0.23, 1.23, 3.20 |
| 67 | " | 0.8% AZC 1% $NH_4Cl$ (+0.1% TAC)* | | | 2280/2600 | >10, >10 |
| 68 | 4% OC-110 | 0.8% AZC | nonylphenol | 3–4 | 2350/2330 | >10, >10 |

*TAC — triallylcyanurate crosslinker added during the emulsion polymerization - 0.1%
**See Table 6 for identification of the surfactants.

TABLE 6

| | |
|---|---|
| OC-20 | Dextrol OC-20, Dexter Chemical Corp - anionic surfactant - complex organic phosphate of polyethoxylated (9-10 units) nonylphenol, a mixture of mono- and diesters. |
| OC-40 | Dextrol OC-40, Dexter Chemical Corp. - anionic surfactant - complex organic phosphate of polyethoxylated (3-4 units) tridecanol, a mixture of mono- and diesters. |
| OC-110 | Dextrol OC-110, Dexter Chemical Corp. - anionic surfactant - complex organic phosphate of polyethoxylated (3-4 units) nonylphenol, a mixture of mono- and diesters. |
| RE-410 | Gafac RE-410, GAF Corp. - anionic surfactant - organic phosphate ester of polyethoxylate (~6 units) nonylphenol. |

EXAMPLE 5

This example shows superior hydrophobic rewet properties are obtained if the phosphate ester surfactant is in the form of a fugitive base salt and at least a portion of the surfactant is present during the polymerization reaction.

In Runs 69-71 an aqueous emulsion was formed of vinyl acetate and an aqueous premix which comprised emulsifying agents and was adjusted to about pH 5 with ammonium hydroxide. The emulsion was charged to a reactor at about 25° C. and pressurized with ethylene to an ethylene-equilibrium pressure of about 330 psi. The ethylene supply was shut off and the addition of the catalyst, activator and acrylic acid delays was commenced at such a rate as to raise the reaction temperature to about 50° C. in a one hour period. The delays were continued maintaining the reaction temperature at 50° C. until the free vinyl acetate monomer content was less than 2% whereupon the reaction was degassed and continued to less than 0.5% free vinyl acetate monomer content.

Table 7 shows the emulsifying agents and post-added surfactant used in each run. Ammonium zirconium carbonate (0.7 wt%) was added in each run. Also given are the results of the Absorption-Reabsorption Test of nonwoven polyester fiber samples bonded with the binder compositions.

Runs 69, 69a and 69b contained hydroxyethylcellulose (1%) and OC-40 phosphate ester (1%) in the polymerization reaction. Run 69a which had OC-40 phosphate ester surfactant post-added in the ammonium salt form yielded absorption and second reabsorption sink times of greater than 10 minutes. Run 69 which had no post-added surfactant and Run 69b which had OC-40 surfactant post-added in the sodium salt form gave much shorter sink times corresponding to inferior hydrophobic rewet properties.

Runs 70 and 70a contained 1% OC-40 surfactant in the polymerization reaction, but only Run 70a had 3% OC-40 surfactant post-added in the ammonium form. Run 70 gave fair sink times of about four minutes while the sink times for Run 70a were all greater than 10 minutes.

Runs 71, 71a, 72 and 72a did not contain a phosphate ester surfactant in the polymerization reaction. No OC-40 phosphate ester surfactant was post-added to either Run 71 or Run 72 while such surfactant was post-added to Runs 71a and 72a. The three sink times for Run 71 were very short (very poor hydrophobic rewet). Run 71a had an excellent initial sink time of greater than 10 minutes but the subsequent two rewet tests showed very short sink times. Run 72 showed good sink times which were improved with post-added phosphate ester surfactant in Run 72a.

The runs demonstrate, in addition to the advantage of using the fugitive base salt of the phosphate ester surfactant, that superior hydrophobic rewet is achieved if at least some of the surfactant is included in the preparation of the interpolymer emulsion.

STATEMENT OF INDUSTRIAL APPLICATION

The invention provides a binder composition for bonding a nonwoven fabric which comprises a phosphate ester or sulfosuccinate half-ester surfactant, an interpolymer of vinyl acetate-ethylene-acrylic acid and a zirconium crosslinking agent. Nonwoven fabrics bonded with such binder compositions are characterized as possessing good tensile strength and good low rewet properties and are especially suited for making the innerliners of disposable diapers.

We claim:

1. A binder composition for nonwoven fabrics which comprises
    (a) an anionic immobilizable surfactant which is a phosphate ester surfactant or a free carboxylic acid group containing surfactant,
    (b) a latex comprising a vinyl acetate-ethylene-olefinically unsaturated carboxylic acid interpolymer colloidally suspended in water, the interpolymer

TABLE 7

| Run | Protective Colloid/ Emulsifying Agents | Acrylic Acid | Tg | Post-Added Surfactant | % Binder Add-On | Absorption/Reabsorption Test (min) |
|---|---|---|---|---|---|---|
| 69 | 1% Hydroxyethylcellulose 1% OC-40 | 3% | +10.5 | none | 50 | 8.0, 0.4, 2.2 |
| 69a | 1% Hydroxyethylcellulose 1% OC-40 | " | " | 3% OC-40 (NH4+ form) | 49 | >10, 3.2, >10 |
| 69b | 1% Hydroxyethylcellulose 1% OC-40 | " | " | 3% OC-40 (Na+ form) | 51 | 2.6, 0.8, 0.5 |
| 70 | 1% Hydroxyethylcellulose 1% OC-40 | " | +11 | none | 50 | 4.5, 4.2, 3.1 |
| 70a | 1% Hydroxyethylcellulose 1% OC-40 | " | " | 3% OC-40 (NH4+ form) | 50 | >10, >10, >10 |
| 71 | 3.0% CO-433 0.5% SVS | " | −3 | none | 50 | 0.1, 0.1, 0.1 |
| 71a | 3.0% CO-433 0.5% SVS | " | " | 3% OC-40 (NH4+ form) | 51 | >10, 0.1, 0.3 |
| 72* | nonionics | ~2.5% | — | none | 48 | 4.5, 9, >10 |
| 72a* | " | " | — | 3% OC-40 (NH4+ form) | 50 | 6.8, >10, >10 |

*A-416 emulsion — a commercial adhesive emulsion of a vinyl acetate-ethylene-acrylic acid interpolymer marketed by Air Products and Chemicals, Inc.

containing about 0.5 to 7.0 weight percent olefinically unsaturated carboxylic acid and sufficient ethylene to provide the interpolymer with a glass transition temperature of from about $-30°$ to $+20°$ C., and (c) a polyvalent metal complex compound.

2. A nonwoven fabric formed from a nonwoven web of fibers bonded together by a binder deposited by saturating the web of fibers with the composition of claim 1.

3. A method for preparing a nonwoven fabric which comprises saturating a nonwoven web of fibers with the composition of claim 1.

4. The invention of claim 1 wherein at least a portion of the surfactant is present in the preparation of the interpolymer latex.

5. The invention of claim 4 wherein substantially all of the surfactant is present in the preparation of the interpolymer latex.

6. The invention of claim 1 wherein the olefinically unsaturated carboxylic acid is an alpha,beta-unsaturated carboxylic acid.

7. The invention of claim 6 wherein the alpha,beta unsaturated carboxylic acid is acrylic acid or crotonic acid.

8. The invention of claim 7 wherein the alpha,beta unsaturated carboxylic acid is about 1 to 5 weight percent of the interpolymer.

9. The invention of clam 8 wherein the alpha,beta unsaturated carboxylic acid is acrylic acid.

10. The invention of claim 6 wherein the interpolymer contains sufficient ethylene to provide it with a glass transition temperature of from about $-5°$ to $+15°$ C.

11. The invention of claim 1 wherein the surfactant is present at about 0.5 to 6 weight percent of the latex solids.

12. The invention of claims 1 or 2 wherein the surfactant is a phosphate ester surfactant.

13. The invention of claim 12 wherein the phosphate ester surfactant is a phosphate ester of a poly(oxyalkylene) alcohol.

14. The invention of claim 12 wherein the phosphate ester surfactant is a phosphate ester of an alkyl or alkylaryl poly(oxyalkylene) alcohol.

15. The invention of claim 12 wherein the phosphate ester surfactant is a phosphate ester of an alkyl or alkylaryl poly(oxyethylene) ethanol.

16. The invention of claim 12 wherein the phosphate ester surfactant is a phosphate ester of tridecyl poly(oxyethylene) ethanol.

17. The invention of claim 12 wherein the phosphate ester surfactant is a phosphate ester of nonylphenyl poly(oxyethylene) ethanol.

18. The invention of claim 15 wherein the surfactant has about 3 to 10 oxyethylene units.

19. The invention of claim 18 wherein the surfactant has about 4 or 5 oxyethylene units.

20. The invention of claims 1 or 2 wherein the surfactant is a sulfoalkanedioic acid half-ester.

21. The invention of claim 20 wherein the surfactant is a sulfosuccinic acid half-ester.

22. The invention of claim 21 wherein the surfactant is an alkyl or alkylaryl polyethoxy sulfosuccinic acid half-ester.

23. The invention of claim 22 wherein the surfactant is an ethoxylated $C_{10}$ to $C_{12}$ alcohol half-ester of sulfosuccinic acid.

24. The invention of claim 1 wherein the polyvalent metal is aluminum.

25. The invention of claim 1 wherein the polyvalent metal is zirconium.

26. The invention of claim 12 wherein the phosphate ester surfactant is a fugitive base salt.

27. The invention of claim 26 wherein the fugitive base salt is an ammonium salt.

28. A binder composition for nonwoven fabrics which comprises (a) a latex comprising a vinyl acetate-ethylene-alpha,-beta unsaturated carboxylic acid interpolymer colloidally suspended in water, the interpolymer containing about 60 to 95 weight percent vinyl acetate, about 0.5 to 7.0 weight percent of an alpha,beta unsaturated carboxylic acid which is acrylic acid or crotonic acid and sufficient ethylene to provide the interpolymer with a glass transition temperature of from about $-30°$ to $+20°$ C., (b) an anionic phosphate ester or sulfoalkanedioic acid half-ester surfactant, the surfactant present at about 0.5 to 6 weight percent of the latex solids, at least a portion of the surfactant present in the polymerization reaction for preparing the latex, and (c) a polyvalent metal complex compound in which the polyvalent metal is aluminum or zirconium.

29. The invention of claim 28 wherein the surfactant is a fugitive base salt of a phosphate ester surfactant.

30. The invention of claim 29 wherein the fugitive base salt is an ammonium salt.

31. A nonwoven fabric comprising a web of nonwoven fibers bonded together with a binder deposited by saturating the web of fibers with the composition of claim 28.

32. The invention of claims 2 or 31 wherein the nonwoven fabric is an innerliner for a disposable diaper.

33. A disposable diaper containing the innerliner of claim 32.

34. A nonwoven fabric bonded by overall impregnation of a nonwoven web of fibers with a binder emulsion containing a sulfoalkanedioic acid half-ester surfactant or a fugitive base salt of a phosphate ester surfactant, an interpolymer containing carboxylic acid units and a polyvalent metal complex compound.

* * * * *